United States Patent
Grise

(10) Patent No.: US 9,889,026 B2
(45) Date of Patent: Feb. 13, 2018

(54) ENDO-URETHRAL PROSTHESIS

(71) Applicant: CENTRE HOSPITALIER UNIVERSITAIRE DE ROUEN, Rouen (FR)

(72) Inventor: Philippe Grise, Rouen (FR)

(73) Assignee: Centre Hospitalier Universitaire de Rouen, Rouen (FR)

( * ) Notice: Subject to any disclaimer, the term of this patent is extended or adjusted under 35 U.S.C. 154(b) by 236 days.

(21) Appl. No.: 14/428,958

(22) PCT Filed: Sep. 18, 2013

(86) PCT No.: PCT/EP2013/069395
§ 371 (c)(1),
(2) Date: Jul. 21, 2015

(87) PCT Pub. No.: WO2014/044718
PCT Pub. Date: Mar. 27, 2014

(65) Prior Publication Data
US 2015/0359645 A1 Dec. 17, 2015

(30) Foreign Application Priority Data

Sep. 18, 2012 (FR) .................................... 12 58756
Jan. 23, 2013 (FR) .................................... 13 50577

(51) Int. Cl.
*A61F 2/82* (2013.01)
*A61F 2/04* (2013.01)
*A61M 25/00* (2006.01)
*A61M 27/00* (2006.01)

(52) U.S. Cl.
CPC .................. *A61F 2/82* (2013.01); *A61F 2/04* (2013.01); *A61M 25/0017* (2013.01); *A61F 2002/047* (2013.01); *A61F 2002/048* (2013.01); *A61F 2002/825* (2013.01); *A61F 2250/0004* (2013.01); *A61F 2250/006* (2013.01);
(Continued)

(58) Field of Classification Search
CPC .......... A61F 2002/825; A61F 2002/047; A61F 2002/048; A61F 2/89
See application file for complete search history.

(56) References Cited

U.S. PATENT DOCUMENTS 5,269,802 A 12/1993 Garber
5,879,370 A 3/1999 Fischell et al.
(Continued)

FOREIGN PATENT DOCUMENTS

DE 2 528 273 10/1976
EP 09/30081 7/1999
WO WO-2011/100263 8/2011

*Primary Examiner* — Katrina Stransky
*Assistant Examiner* — Daniel Bissing
(74) *Attorney, Agent, or Firm* — Blakely Sokoloff Taylor & Zafman LLP

(57) ABSTRACT

An endo-urethral prosthesis characterized in that it comprises a set of guides (100) defining an internal space (201) in a urinary channel, and one or more support elements (110) for supporting the internal wall of the urinary tract, the guides comprising recessed areas and protruding areas, said protruding areas forming locking regions (21) for holding the support elements in place, in a position that allows them to support the internal wall of the urinary tract.

10 Claims, 3 Drawing Sheets

Figure 1:
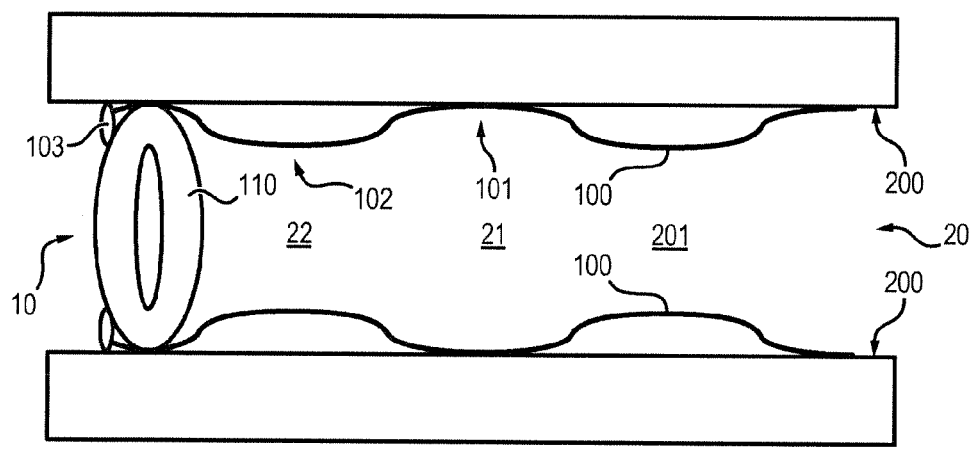

(52) U.S. Cl.
 CPC ............... *A61F 2250/0039* (2013.01); *A61F 2250/0059* (2013.01); *A61M 27/008* (2013.01)

(56) References Cited

U.S. PATENT DOCUMENTS

| | | | |
|---|---|---|---|
| 5,897,589 A * | 4/1999 | Cottenceau | A61F 2/07 623/1.13 |
| 2001/0021835 A1 | 9/2001 | Mitchell et al. | |
| 2004/0193283 A1 | 9/2004 | Rioux et al. | |
| 2011/0264186 A1 | 10/2011 | Berglung et al. | |

* cited by examiner

ENDO-URETHRAL PROSTHESIS

FIELD OF THE INVENTION

The present invention relates to a endo-urinary prosthesis, i.e. an prosthesis intended to keep open a urinary channel such as the urethra or the ureter.

The ureter is a channel carrying urine from the bassinet toward the urinary bladder.

The urethra is the urinary channel situated below the urinary bladder. It carries urine during urination towards the meatus located at the end of the penis in a man. This channel has the peculiarity of being longer in men than in women.

These channels are exposed to pathologies such as reduction in their internal diameter by a process of fibrosis.

Shrinkage can be treated so as to restore the internal diameter of these channels, but they often relapse.

Another pathology is the abnormal closure of the sphincter during urination by anomaly of the neurological control, called detrusor-external sphincter dyssynergia, which has the effect of blocking urination partially or totally.

BACKGROUND OF THE INVENTION

Several methods are known for limiting these pathologies.

The two treatments most frequently used are self-catheterization and the use of endo-urinary prostheses.

Self-catheterization by the patient with a catheter of large diameter, regularly, is often painful, poorly tolerated, exposed to urinary infections; moreover certain patients cannot or do not wish to self-catheterize. Sounding by a nurse or a physician is limiting and expensive, thus this is rarely carried out over a long term.

The other process used is the placement of an endo-urinary prosthesis which keeps open the inner diameter of the urinary canal to be treated, over a duration which can be long or even permanent.

To this end, endo-urethral prostheses have been used, intended to be placed in the urethra, and endo-ureteral, intended to be placed in the ureter.

A first type of endo-urinary prosthesis known is a cylinder made of mesh, generally metallic, interlaced or in the form of a screen.

Such a cylinder is introduced into the urethra to apply a pressure on its wall. In one well-known configuration such a cylinder is introduced into the urethra with a small diameter, then is expanded radially (which causes shortening of the cylinder). In the expanded state of the cylinder, its mesh is putting pressure on the ureteral mucosa.

Once in place, these prostheses gradually incrust in the wall of the urethra which, with time, covers the prostheses.

This inlay of prostheses in the wall of the urethra makes it very difficult to remove them when that is desired. Moreover, these prostheses can be sources of complications such as a fibrous or polypoid reaction within the prosthesis or at its ends.

The second type of endo-urinary prosthesis is a cylinder made of a metal wire rolled into a continuous joined coil.

Such a prosthesis is generally considered to be temporary and it is typically intended to remain in place in the urethra for duration lasting up to a few months.

The wire has a shape memory such that the diameter of the cylinder is reduced when cold, and greater when hot. It is thus possible to dilate the diameter of the prosthesis, but only to a limited degree.

Thus, it is possible to heat locally the parts of such a cylinder after its placement in the urethra (typically at both ends), to dilate those parts with the aim of avoiding migration of the prosthesis.

However in certain urethras, particularly large and flexible urethras, the prosthesis doesn't have enough push on the wall and it is possible that it will migrate, most often toward the urinary bladder.

Moreover, the configuration with jointed coils of such a prosthesis has a considerable surface area, suitable for attachment of solidified urine. The result is that such prostheses are likely to frequently be obstructed by calcifications, and it is therefore necessary to change them regularly when the intended purpose is a long-range effect.

A known endo-urinary prosthetic, called "double J" is a flexible tube curved at both ends, so as to ensure its being held. One end is housed in the kidney and the other in the urinary bladder.

However, such a prosthesis extends the entire length of the ureter and can thus provoke a feeling of discomfort in the patient. Alternatively, a metal prosthesis with or without thermal dilation can be considered, but is indicated only in precise and limited case (fibrosis, benign or malignant, inside or on the outside of the ureter, and a counter-indication for surgery).

The invention intends to provide a solution overcoming one or more of the disadvantages mentioned above.

DISCLOSURE OF THE INVENTION

To this end, the invention proposes according to a first aspect an endo-urinary prosthesis characterized in that it includes a set of guides defining in a urinary channel an internal space, and one or several elements of support to support the inner wall of the urinary channel, the guides including locking regions for maintaining in place the support elements, in a position which allows them to support the inner wall of the urinary channel.

Preferred but not limitative aspects of this prosthesis are the following:
  the guides include recessed areas and protruding areas, said protruding areas including locking regions of the guides,
  the guides are corrugated rods,
  the support elements are ring shaped,
  the rings have a variable diameter.

Figure 2A:
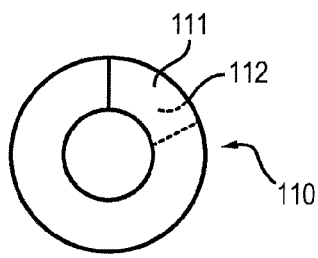
Figure 2B:
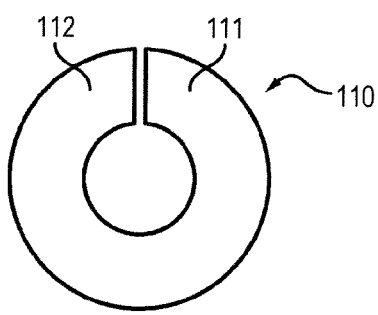
Figure 3:
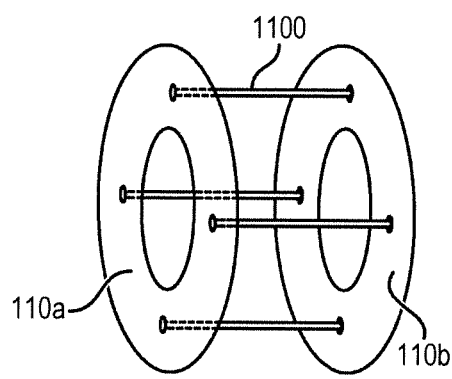
Figure 4:
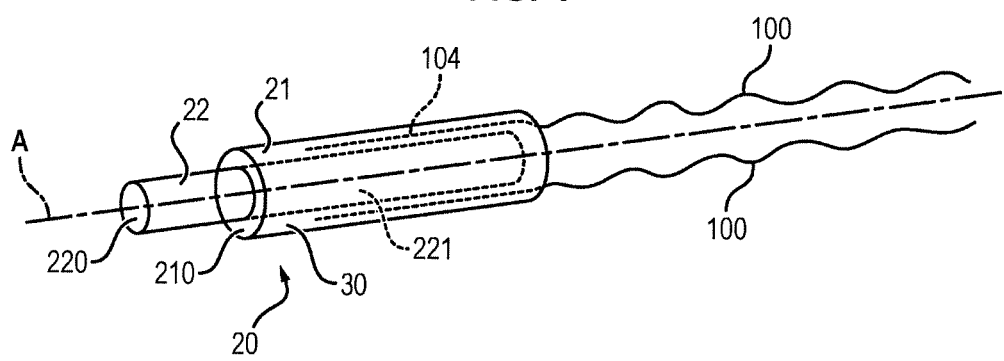

Other aspects, aims and advantages of the invention will be revealed as a result of reading the following description of preferred embodiments of the invention, made with reference to the appended drawings on which are:

FIG. 1 shows schematically a prosthesis according to a first embodiment of the invention, engaged in a urinary channel represented here in longitudinal section, FIG. 2 shows a ring of a prosthesis according to the invention, in a compressed (FIG. 2a) and expanded (FIG. 2b) position, FIG. 3 shows a pair of rings capable of being implemented in a prosthesis according to a second embodiment of the invention, FIG. 4 represents a placement tool for placing a prosthesis according to the first embodiment of the invention.

Figure 5A:
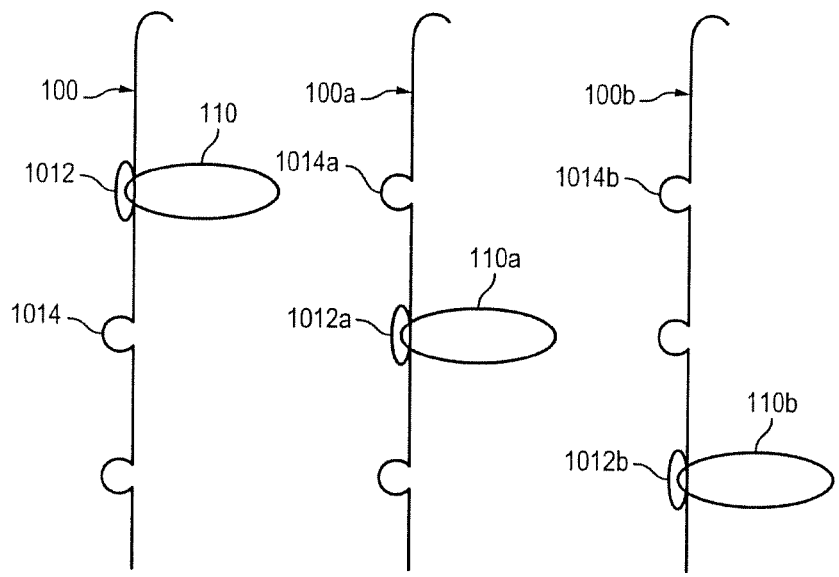
Figure 5B:
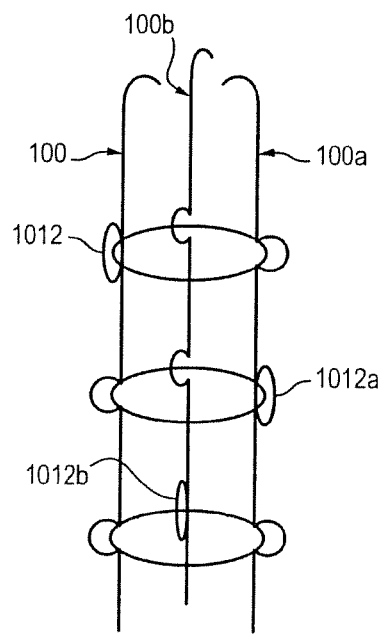

FIG. 5a shows a prosthesis according to a third embodiment of the invention, including several parts and in an un-assembled state, FIG. 5b shows the prosthesis of FIG. 5a in an assembled state.

With reference to FIG. 1, a prosthesis 10 according to a first embodiment of the invention is engaged in a urinary channel 20 of which the wall 200 is visible in the figure.

On this figure, the urinary bladder and the distal end of the prosthesis are situated to the left side. The proximal end of the prosthesis is situated on the right side.

The prosthesis includes guides 100 and one or more rings 110. In FIG. 1, a single ring 110 is visible. In practice the prosthesis will include several rings.

The prosthesis can include typically three guides, or more. The guides are not linked together, each guide being independent of the other guides.

The guides are typically made of metal.

The guides, which extend both in the longitudinal direction of the channel, defining between them an inner space (201) which, when the rods are in place, extend into the urinary channel.

The length of the channels is adapted depending on the length of the urinary channel to be opened.

In the embodiment shown in the figure the guides are rods.

It is noted that the rods 100 are not perfectly rectilinear. On the contrary, these rods have a shape that presents protruding areas 101 and recessed areas 102.

In the mode of realization illustrated in FIG. 1, the rods also have a corrugated form.

Each rod has a distal extremity 103 made to conform to the opening of the urinary channel.

The protrusions of the different rods are placed facing each other. This defines in a urinary channel the "protruding areas" 21 in the space surrounded by protrusions of rods.

Likewise, the recesses of the different rods are placed facing one another. This defines in the urinary channel the "recessed areas" 22 in the space surrounded by the recesses of rods.

The rods have been brought into the urinary channel in a manner which will be disclosed later.

The ring 110 is positioned in a protruding area. Its diameter corresponds to the diameter of this area.

The rods were introduced in a first time period into the urinary channel, and positioned so as to constitute the internal space 201, and the areas 21 and 22.

Once the rods are positioned, each ring is then engaged in the internal space 201, until it is found facing a protruding area 21 wherein it is desired to position the ring.

For that it is necessary that the ring cross the recessed areas 22, the diameter whereof is less than the diameter of the protruding areas 21.

In order for this crossing to occur, it is possible to force the ring through the recessed area. In this case, the guides will temporarily move away during passage of the ring, by pushing away the walls of the urinary channel, which has a certain elasticity.

Once the ring is in place in the protruding area desired, the ring is held in this area by cooperation of shapes with the contours of the protruding area which captures the ring.

Thus, the embodiments of the invention wherein the guides 100 have protruding areas and recessed areas constituting a manner of forming, on the guides, locking regions of the rings. It is possible to form these locking regions in another manner, for example by realizing notches in the guides, etc.

In every case, the locking regions make it possible to maintain in place the rings, in a position which will allow them to support the inner wall of the urinary channel.

Thus, the rings have, in the embodiment illustrated on these figures, a particular shape of support elements.

It will be possible to position a ring per protruding area, or leave one or several protruding areas without a ring, or on the contrary place two rings or more in a single protruding area, depending on the structure that is sought.

In this regard, the prosthesis according to the first embodiment of the invention is highly modular, and can easily be adapted to the needs of each particular case. This derives in particular from the fact that each guide and each ring is a distinctive element, separated from the others and which is not linked to it in the structure of the prosthesis.

If a particularly strong framework is sought, it will also be possible to provide rings with different thicknesses, depending on what is needed.

According to an advantageous variant, it is also possible to provide that the diameter of the ring is variable between a reduced diameter and an expanded diameter, and to give the ring its expanded shape only when the ring is facing the desired protruding area.

For that purpose, one can for example provided that the ring 110 is a broken ring, such as that shown in FIGS. 2a and 2b.

Such a ring is not closed: it is constituted of a rolled metal ribbon.

In FIG. 2a, the ribbon is rolled compressed and the ring has a reduced diameter. The two ends 111, 112 of the ribbon cover one another.

On FIG. 2b, the ribbon is rolled without being compressed and the ring has an expanded diameter. The two elements of the ribbon do not cover one another.

To pass from the compressed configuration to the non-compressed configuration, it is possible to use simply the elasticity of the compressed ring.

In this case, during positioning of the ring in the urinary channel, the ring will be kept compressed during its passage of the recessed areas. Once the ring is in position in the desired protruding area, the compression on the ring is released, which then takes its expanded diameter and remains in place in the protruding areas, the contours of which hold the ring in place.

It is also possible to provide other means to make the diameter of the ring vary. It is possible, for example, to employ shape memory alloys for example.

The end 103 of each rod, curved, allows to:
hold in place the most distal ring (that which is illustrated in FIG. 1), the distal ring being inserted or integral from the beginning with the distal end of the rods;
supply an anti-inflammation buffer particularly during introduction of the rods.

The shape of the rods, with its protrusions and recesses, makes it possible in particular to:
constitute protruding areas to position and retain the rings,
avoid the migration of the prosthesis. Indeed, the wall of a urinary channel is generally flexible and after the placement of the prosthesis this wall will come into contact with the rods, including at the recessed areas. The parts of the wall of the urinary channel in contact with the rods at the recessed areas thus makes it possible to lock the rods and therefore the prosthesis.

The configuration of the prosthesis according to the invention has the advantage of minimizing the zone of contact between the prosthesis and the urinary channel wall.

The prosthesis according to the invention also makes it possible to calibrate in the urinary channel a large opening diameter. This prosthesis is not in fact associated with any diameter limitation, its diameter being determined by the selection of the rings which are chosen to keep open the urinary channel and exert pressure on its wall.

It is thus possible to easily and with great accuracy adapt each prosthesis to the internal diameter of the urinary channel to be treated.

The prosthesis according to the invention is easy to put into place, but also easy to withdraw. It is enough in fact to disassemble a prosthesis according to the invention, placed in a urinary channel, by carrying out the inverse operations to those carried out for placing them, to realize easy ablation of the prosthesis.

Thus, unlike screened prostheses which incrust progressively into the wall and became very difficult to extract, the prosthesis according to the invention is easily dismountable by ablation of the rings, then of the rods.

Unlike known prostheses, in particular the coiled prostheses with thermal shape memory, which have a great prosthetic surface exposed to calcium inlay, the prosthesis according to the invention has a small surface exposed to calcifications of the urine.

The endo-urinary prosthesis described previously is suited to placement in the urethra or also in the ureter. In any case, care will be taken to adapt the dimensions of the prosthesis to the dimensions of the urinary channel wherein the prosthesis is intended to be placed.

A few specifics will now be given on the means of placing a prosthesis according to the invention in a urethra, and on a device which, according to the invention, allows such a placement.

The prosthesis is put in place by an endoscopic surgical intervention.

The localization of the area of the urethra to open and its length have been determined previously.

The diameter of the area of the urethra to be opened is determined pre-operatively, by introduction of a catheter of calibrated diameter and/or by endoscopic vision. This diameter conditions the size of the rings of the prosthesis, which will take on the same diameter.

As was already mentioned, the set of rods is introduced and positioned in a first time period, and the rings are then positioned—and in some cases dilated—with regard to the protruding areas desired.

To introduce and position the rods in the urethra, it is possible to use a placement tool such as that shown in FIG. 4, even though this is a non-limiting example. On this figure the distal end is to the right, the proximal to the left.

This tool 20 includes a hollow tube 21, coaxial with a full bar 22, held fixedly to the tube in one embodiment.

The bar 22 is for example fixed in an end wall 210 of the tube. It is possible to provide for other means to make the bar integral with the tube, for example an O-ring between these two elements.

The bar 22 extends within the hollow tube to define between the bar and the internal hollow a space 30.

In this space 30 were fixed the proximal ends of the rods 100. These ends terminate the proximal sections of the rods, sections which are straight to allow their engagement in space 30.

The proximal extremities of the rods 100 were fixed in the space 30 (by any suitable means) so that they:
  position each rod 100 coaxially with the tool 20,
  position in a desired manner each rod 100 in a desired place of the annular space 30, so as to distribute the rods 100 in a desired manner about the annulus formed by this space. Typically, the rods are distributed regularly on the surroundings of the space 30,
  position the rods in such a manner that their distal ends are facing one another,
  position the protruding areas and the recessed areas facing each other. It is specified that, for all the rods the protruding areas and the recessed areas are distributed in the same manner along the rod.

The tool 20 is placed at the end of the urethra and partly outside the urethra, the distal extremities of the rods being engaged in the urethra. It is possible to provide for the distal extremity of the tube 21 to also be engaged in the urethra.

The tube 21 can be transparent.

Moreover, to guarantee a good longitudinal operation of the rods during their introduction into the urethra, it has been possible to advantageously provide areas of the end of the tool 20 which remained outside the urethra.

Indeed, the tube 20 being integral with the rods it is possible, by having marked before introduction into the ureter a benchmark on the outer wall of the tool, to see for example that the rods were introduced by the correct length into the urethra when the benchmark is at the end of the penis.

Once the rods 100 are positioned in the desired manner in the urethra, and these rods being constantly integral with the tool 20, it is possible to position the rings in the protruding areas.

To place the rings it will be possible for example to engage rings in the proximal end 220 of the bar 22.

To this end, the bar is hollow and allows passage of the rings in the channel 221 which runs through the bar longitudinally, from end to end.

The rings can be pressed along the channel by any suitable means, for example a plug sliding in the canal.

It is also possible to provide at the center of the channel 221 and on the symmetry axis A of the tool a longitudinal guide (not shown) about which the rings are slid on, and the distal end whereof extends right up to facing the desired protruding area for the ring currently being placed.

Such a longitudinal guide can be mounted sliding with respect to the bar 22. In this manner, it is possible to adjust the position of its distal end in the urethra, with and to the degree of the progression of placement of the rings. It is noted that the rings will be placed starting with the most distal and ending with the most proximal.

As was mentioned, it is possible that the rings are elastically constrained radially toward their center, to preserve a reduced diameter, as long as they are not positioned in their desired protruding area. To this end, the channel at the center of the bar can have the same reduced diameter, to keep the rings compressed as long as they are introduced into the channel.

In that case, the distal extremity of the bar can be positioned facing the protruding area desired.

This can be obtained with a longer bar that that shown in the figure, and by gradually withdrawing the tool by placing the rings one after the other so as to position the extremity of the bar less and less far into the urethra. In such a case, the rods 100 will have been separated from the tool 20 (for example by cutting the rods by some suitable openings in the wall of the hollow tube 21, or by any other means of separation such as the freeing of blockage means which held the rods fixed in the space 30).

This can alternatively be obtained by a bar 22, which is not fixed with respect to the tube 21, but on the contrary can slide with respect to it. In this case, the bar is progressively withdrawn during placement of the rings, with having necessarily separated the rods 100 from the tool 20 previously.

In every case, it is certain that each ring is positioned and freed with regard to the desired protruding area.

Once freed, in the case where the ring was being radially constrained, it extends to take on its expanded diameter.

In all cases, including if the ring was forced through some recessed areas which are elastically and temporarily separated to allow the ring to pass, once the ring is in place in the desired protruding area it is held there by shape cooperation with the rods 100.

Once the rings are in place the central guide is withdrawn, if the device included one.

If the rods were not already separated from the tool 20, that separation is executed.

In any case after this separation the tool 20 is withdrawn.

The prosthesis, including the rods and the rings in place, is then positioned in the urethra.

The tool 20 can also be used for the placing of the endo-urinary prosthesis in another urinary channel than the urethra, for example in the ureter.

The guides and/or the support elements can be made in a thermally sensitive material, for example Nitinol, to allow an insertion of the prosthesis into a cylinder, and an expansion by retraction of the insertion cylinder. The diameter of the Nitinol rods will be sufficient to give a good holding and radial resistance under compression.

In a first embodiment of the prosthesis which as described previously, the support elements (the rings) are movable with respect to the guides (the rods). This mobility of the rings with respect to the rods makes possible an insertion in the urinary channel. This mobility also allows the insertion of a more or less large number of rings depending on the type of channel wherein the prosthesis must be inserted, and allows a modular positioning of the rings along the prosthesis in the corresponding protruding areas: the prosthesis can then be adapted to a large variety of urinary channels and the rings can be locked to well targeted positions in the urinary channel where it must imperatively be kept open.

However, certain other embodiments are also possible.

As illustrated in FIG. 3 it will also be possible to use, in a second mode of embodiment of the prostheses, pairs of rings 110a, 110b, consisting of two rings connected by spacers 1100, to minimize the contact surfaces. It is also possible to constitute in this manner triple, etc. rings connected by spacers.

In a third embodiment alternative of the prosthesis according to the invention (illustrated on FIGS. 5a and 5b), each rod thus comprises at least one permanent locking region which is integral with a ring, the permanent locking region being localized at a longitudinal position which is proper to it (any other characteristic of the rods and/or the rings according to the first embodiment being taken up again in the prosthesis according to the third embodiment).

Defined here as a permanent locking region of a guide is a permanent connection allowing retention of a ring attached to the guide even before insertion of the guide and of the ring into a urinary channel. This connection can introduce or not an articulation between the rods and the integral ring.

This permanent connection can be a weld near a protruding area, which maintains the ring in one transverse direction with respect to the corresponding rod.

This permanent connection can alternatively be obtained by an opening created in a rod, the opening having part of the ring passing through it. Such an opening allows mobility, at least in rotation, of said ring compared to an axis that is normal to that opening. The coiling can include one turn of the rod around the ring, or even several turns.

This opening can for example be obtained by coiling a rod around a portion of the ring, and constitutes a particular protruding area of one rod.

The opening thus defined around the ring can present an inner perimeter substantially equal to the outer perimeter of the coiled portion of the ring, so as to reduce the dimensions of this opening.

As a variant, the opening defined by the coiling of the rod around the ring can extend longitudinally and have a greater perimeter on the outside of the portion of ring that is coiled (for example, the opening can have an oval form with the large diameter oriented longitudinally). Such an orifice makes it possible to allow a mobility of the ring coiled in translation longitudinally with more than one mobility of that ring in rotation, without increasing the thickness of the rod, and therefore not the thickness of the prosthesis in one radial direction, after assembly of several rods.

The rods are adapted so that each permanent locking region of a rod is facing non-permanent locking regions of other rods.

Thus, the prosthesis can be formed by assembly of several parts, each part being formed by a rod and a ring which is integral with it.

Each weld of a ring to a respective rod makes it possible to confer to the prosthesis, after assembly, a minimal rigidity in the longitudinal direction of the prosthesis.

For example, the prosthesis illustrated in FIGS. 5a and 5b includes a first rod 100, a second rod 100a and a third rod 100b, each rod including a succession of three locking regions having respectively a first, a second and a third longitudinal position.

The first rod 100 comprises a first permanent locking region 1012 localized at the first longitudinal position and integral with a first ring 110. The second rod 100a comprises a second permanent locking region 1012a localized at the second longitudinal position and integral with a second ring 110a. The third rod 100b comprises a third permanent locking region 1012b localized at the third longitudinal position and integral with a third ring 110b.

Thus, the ring connected with each rod can be accommodated in non-permanent locking zones of the other rods which are localized at the same longitudinal position.

In this third mode of realization, the rods are rectangular. Each non-permanent locking region 1014, 1014a, 1014b is a protruding area having the shape of an open oval ring of dimensions suitable to receive the ring 110, 110a, 110b respectively.

Each non-permanent locking region includes an opening extending along the rods along a length adapted to allow a portion of the insertion of the ring in the protruding area by forced separation of the edges of this opening, and on the other hand to retain the ring in the protruding area, after an elastic return of the edges.

The insertion of the ring in the protrusion on its other rods allows giving a certain flexibility of curvature while still guarding the shape and the resistance of the prosthesis after assembly. The prosthesis can then also be positioned comfortably in a single urinary channel not perfectly rectilinear, which still conserves a rigidity applied by the fact of having welded each rod to a respective ring.

The diameter of each protruding area of a non-permanent locking region can be selected to be greater than the diameter of the ring to be accommodated, so as to give the prosthesis mobility after assembly.

Z-shaped protruding areas can also be added on the rods, in the case where it might give better flexibility to the prosthesis.

Moreover, each permanent locking region 1012, 1012*a*, 1014*b* is also a protruding area having the shape of an oval open ring with dimensions adapted to receive the ring 110, 110*a*, 110*b* respectively.

The three rods can be equidistant one from the other over a transverse circular section, or be distributed differently if more flexibility is to be given to a particular axis.

Of course, the second embodiment can be extended to N rods each including at least N locking regions of which at least one permanent locking region, N being greater than or equal to 3.

The fact of having more than N locking regions on each of the N rods makes it possible to allow the consolidation of the prosthesis by means of additional mobile rings.

In a fourth embodiment (not illustrated), at least one of the rings is integral with each rod, and articulated or not at each rod.

This integral ring can be the distal ring, that is the ring placed in the protrusion closest to the distal end of the prosthesis, the proximal ring, that is the ring placed in the protrusion closest to the proximal end of the prosthesis, and/or any intermediate ring localized between the distal ring and the proximal ring, in the case where the prosthesis includes several rings.

The integral character of rings preferably articulated, makes it possible in particular to facilitate insertions of the rods. The rods can in fact be inserted into a urinary channel while the at least one integral ring is in a folded position. In addition, the rods can be put into shape by positioning the integral rings in a deployed position, that is in a position intended to keep the urinary channel open.

In one particular variant of this fourth embodiment, each locking region is a permanent locking region, integral with a ring. N being the number of rods in the prosthesis, each ring is then connected permanently to N rods, depending on the connections already described in reference to the second embodiment (weld, orifice obtained by coiling, etc.).

For example, each connection between a ring and a rod can be obtained by coiling, each coiling defining the oval orifice extending longitudinally described previously.

The prosthesis thus obtained is thus entirely articulated, and each ring of the prosthesis is movable in longitudinal translation with respect to the rods. The rods can thus be positioned in a urinary channel, before adjusting more finely the positioning of each ring with respect to the rods in this same channel.

The rings illustrated in FIGS. 2*a* and 2*b* can be included in the third and second embodiments of the prosthesis described.

The invention claimed is:

1. An endo-urinary prosthesis comprising a set of guides extending along a longitudinal axis and defining in a channel an inner space, and several support elements to support an inner wall of the channel, wherein each support element is mobile with respect to at least one of the guides, wherein the guides comprise recessed areas and protruding areas, said protruding areas constituting locking regions to maintain in place the support elements, in respective positions spaced apart from one another along the longitudinal axis in the inner space, wherein the support elements support the inner wall of the channel.

2. The prosthesis according to claim 1, wherein each guide comprises at least one permanent locking region which is integral with a respective support element.

3. The prosthesis according to one of claims 1 or 2, wherein the guides each have a succession of locking regions localized at a same longitudinal positions, the longitudinal positions of the permanent locking regions being different.

4. The prosthesis according to claim 1, wherein the recessed areas are straight rods and that each protruding area constituting a locking region has an open-ended ring shape.

5. The prosthesis according to claim 1, wherein the support elements are rings.

6. The prosthesis according to claim 4, wherein each guide is coiled around one portion of a respective ring.

7. The prosthesis according to claim 5, wherein the rings have a variable diameter.

8. The prosthesis according to claim 1, wherein at least one of the guides and the support elements is made of a thermosensitive material.

9. The prosthesis according to claim 1, wherein at least one of the guides and the at least one ring is made of Nitinol.

10. The prosthesis according to claim 5, wherein the guides extend along a longitudinal axis, and wherein the position wherein the rings support the wall of the channel are transversal positions relative to the longitudinal axis.

\* \* \* \* \*